United States Patent
Linder et al.

(10) Patent No.: US 11,446,071 B2
(45) Date of Patent: Sep. 20, 2022

(54) RESILIENT FASTENER WASHER

(71) Applicant: Curiteva, Inc., Tanner, AL (US)

(72) Inventors: Eric Linder, Columbus, OH (US);
Ryan Heskett, Wellington, FL (US)

(73) Assignee: Curiteva, Inc., Tanner, AL (US)

( * ) Notice: Subject to any disclaimer, the term of this patent is extended or adjusted under 35 U.S.C. 154(b) by 170 days.

(21) Appl. No.: 16/983,035

(22) Filed: Aug. 3, 2020

(65) Prior Publication Data
US 2022/0031374 A1   Feb. 3, 2022

(51) Int. Cl.
| | |
|---|---|
| *A61B 17/86* | (2006.01) |
| *F16B 31/02* | (2006.01) |
| *F16B 39/24* | (2006.01) |
| *A61B 17/88* | (2006.01) |
| *A61B 17/84* | (2006.01) |
| *A61B 17/00* | (2006.01) |

(52) U.S. Cl.
CPC ........ *A61B 17/8695* (2013.01); *A61B 17/846* (2013.01); *A61B 17/8875* (2013.01); *F16B 31/028* (2013.01); *F16B 39/24* (2013.01); *A61B 2017/00526* (2013.01); *A61B 2017/00862* (2013.01)

(58) Field of Classification Search
CPC .......................... A61B 17/8695; A61B 17/8047
See application file for complete search history.

(56) References Cited

U.S. PATENT DOCUMENTS

| | | | |
|---|---|---|---|
| 1,547,162 | A | 7/1925 | Bohlman |
| 1,793,453 | A | 2/1931 | Barili |
| 3,062,557 | A | 11/1962 | Cyril |
| 4,988,351 | A | 1/1991 | Paulos et al. |
| 5,201,627 | A | 4/1993 | Biedenbach |
| 6,228,087 | B1 | 5/2001 | Fenaroli et al. |
| 6,231,606 | B1 | 5/2001 | Graf et al. |
| 7,198,445 | B2 | 4/2007 | Kramer |
| 7,615,069 | B2 | 11/2009 | Paul |
| 8,475,502 | B2 | 7/2013 | Paul |
| 8,998,968 | B1 | 4/2015 | Brow |
| 2005/0015131 | A1* | 1/2005 | Fourcault ........... A61B 17/7059 607/116 |
| 2005/0260061 | A1 | 11/2005 | Sung |
| 2012/0010669 | A1* | 1/2012 | O'Neil ............... A61B 17/8695 606/305 |

* cited by examiner

*Primary Examiner* — Olivia C Chang
(74) *Attorney, Agent, or Firm* — Davikd L King

(57) ABSTRACT

A resilient washer has a one-piece washer body. The washer body has a central opening, an upper fastener interfacing section or bowl, a lower structure interfacing section or bowl and a resilient middle portion. The resilient middle portion connects the upper fastener interfacing section or bowl and the lower structure interfacing section or bowl. The resilient middle portion is configured to be locally collapsed when a fastener in the central opening is tightened into a structure. In one embodiment, the upper fastener interfacing section or bowl is annular, wherein the upper fastener interfacing section or bowl has a concavity for holding a head of the fastener. The concavity can be of a hemispherical shape. Preferably, the concavity has a smooth surface to allow polyaxial movement of a fastener.

28 Claims, 11 Drawing Sheets

RESILIENT FASTENER WASHER

FIELD OF THE INVENTION

The present invention relates to washers for mechanical fasteners generally, more particularly for a resilient washer.

BACKGROUND OF THE INVENTION

The use of washers in combination with fasteners is well known. The most common washer is a flat washer with an opening in the center and of a disc shape that provides an enlarged surface area to abut the head of a fastener when the fastener is tightened. This enlarged contact area creates a compression between the structures to be joined together. The washer, at the exterior surface of a structure to be joined, provides an area against which the distal end of the fastener, preferably with threads, can pull against as it is being tightened to join the two elements. This creates the ability to more securely fasten the two structures together.

A modification to the flat washer is commonly called a lock washer. This is a similar disc shape, but with a split and a bend or twist in the washer such that the ends at the split do not align, and as the head of the fastener or screw is tightened, this pulls the washer into tight compression, not only aligning the ends, but also creating a spring like resistance against the head of the screw. This is helpful in preventing a fastener from becoming dislodged due to vibration or a relaxing of the materials being joined. Lock or spring washers are also well known and commonly used.

In U.S. Pat. No. 5,201,627 entitled "Washer for Screws", a washer of an annular shape with an inverted "U" shaped cross section with at least one cutting edge is designed to fasten a wood screw tightly into wood. As the screw is pulled tightly against the washer, the washer penetrates into the wood creating a localized compression of the wood material and helps the screw hold the wood tightly against the structure it is to be joined to. This type of washer not only increases the surface area, but also creates a compression of the wood to prevent splitting.

The objective of the washer is not only to provide an increased ability for the fastener to tighten against the structure against which it is being placed, but also in the case of locking washers to provide a spring like resistance to loosening.

The present invention is a unique washer which provides these features that allows for localized compression or collapse creating a spring force locally around the periphery of the washer as described hereinafter.

SUMMARY OF THE INVENTION

A resilient fastener washer, or resilient washer, has a one-piece washer body. The washer body has a central opening, an upper fastener interfacing section or bowl, a lower structure interfacing section or bowl and a resilient middle portion. The resilient middle portion connects the upper fastener interfacing section or bowl and the lower structure interfacing section or bowl. The resilient middle portion is configured to be locally collapsed when a fastener in the central opening is tightened into a structure.

In one embodiment, the upper fastener interfacing section or bowl is annular, wherein the upper fastener interfacing section or bowl has a concavity for holding a head of the fastener. The concavity can be of a hemispherical shape. Preferably, the concavity has a smooth surface to allow polyaxial movement of a fastener. The upper fastener interfacing section or bowl has an annular rim at a proximal end with a plurality of spaced grooves that aid in the retention of the washer to a fastener.

In this embodiment, the lower structure interfacing section or bowl is also annular, wherein the lower structure interfacing section or bowl has a distal end for engaging a surface of a structure to be fastened. The distal end is contoured having a plurality of elongated peaks spaced by shallow troughs wherein the peaks first contact the surface of the structure to be fastened and the shallow troughs contact thereafter as the fastener is tightened wherein the distal end can be tapered or inclined toward the central opening.

The middle portion has a plurality of columns connecting the upper and lower structure interfacing section or bowls. Each pair of the plurality of columns is spaced by an enclosed slotted opening forming a plurality of enclosed slotted openings. Upon tightening of the fastener to the structure, a portion of each enclosed slotted opening locally collapses bringing the lower structure interfacing section or bowl and upper fastener interfacing section or bowl closer in proximity adjacent the collapsed portion of the enclosed slotted opening. Each of the enclosed slotted openings extends arcuately between columns and the collapse of each of the enclosed slotted openings occurs midway between the columns.

In a preferred embodiment, each peak of the distal end is located midway between a pair of adjacent columns and centered under a slotted opening. Each column is positioned above a midway location of each shallow trough. The resilient washer has four columns and four slotted openings in the middle portion. The washer body of the resilient washer is made of metal, wherein the metal is one of steel, stainless steel, titanium, aluminum or alloys of each. Alternatively, the washer body of the resilient washer can be made of other materials such as plastic.

BRIEF DESCRIPTION OF THE DRAWINGS

The invention will be described by way of example and with reference to the accompanying drawings in which.

DETAILED DESCRIPTION OF THE INVENTION

Figure 1:
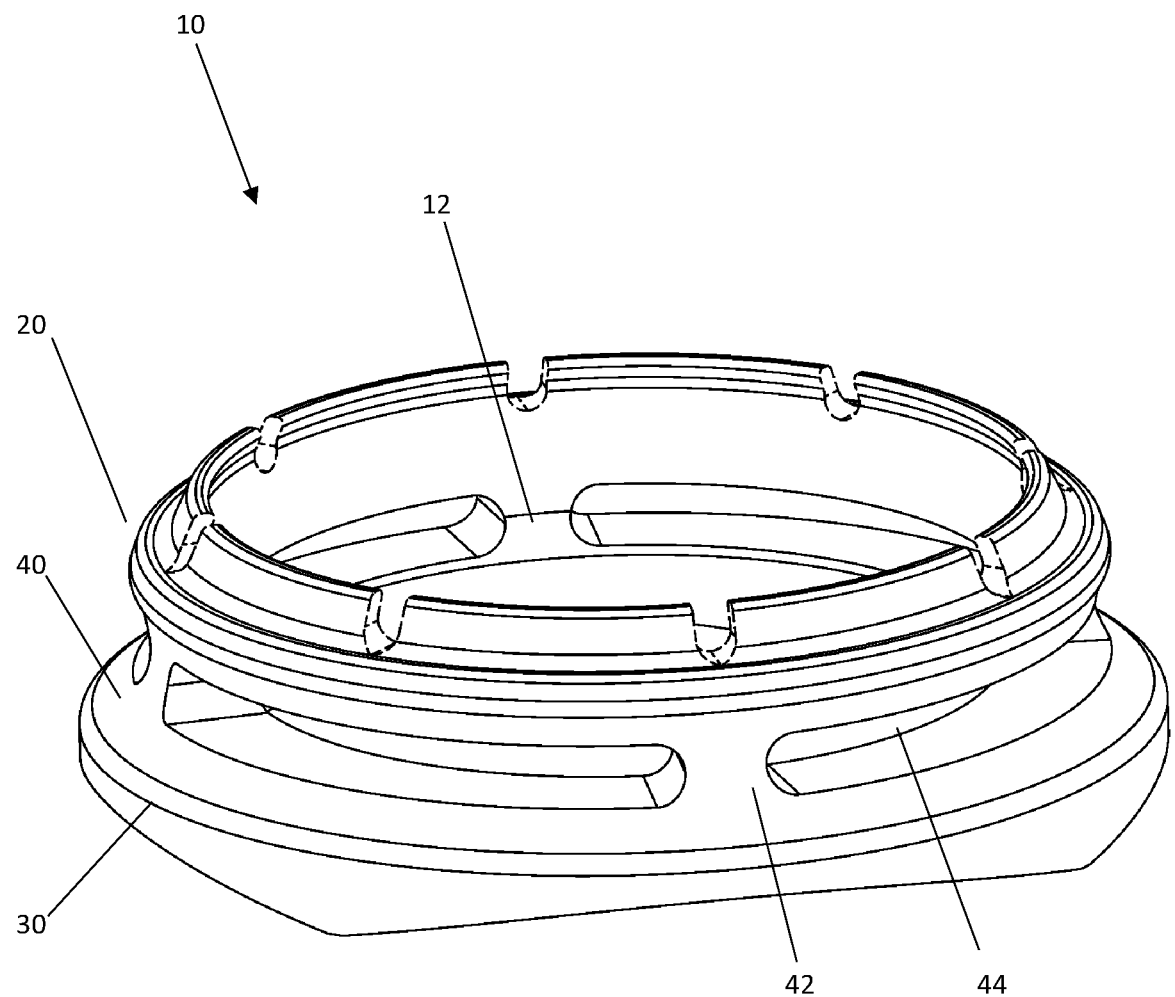
FIG. 1 is a perspective view of the resilient washer of the present invention.

The present invention resilient washer 10 has a unique one-piece structure having a top portion for supporting a head of a fastener and a bottom or base portion for engaging an outer surface of a material being fastened to another material and a resilient compressible middle portion interposed between the top and bottom portions. The bottom or base portion, when the fastener is tightened, provides a compressive spring force into the material being fastened and also back against the head of the fastener in the direction opposite of the tightening force. This resistive spring back force creates an anti-loosening feature when the fastener is tightened. The compressive spring force can be tuned by increasing or decreasing the thickness of the washer, and or varying the quantity, size, and shape of the washer elements, particularly in the lower bottom portion or the middle portion. Changes in stiffness can increase or decrease the compressive spring force. In the illustrated embodiment described below, the middle portion has columns connecting the top portion to the bottom or base portion. These columns are each spaced by an elongated slot or opening. The columns can be tuned by varying the quantity and/or dimensions such as the height, width or thickness or even the shape. As illustrated, each column has an arched top or bottom. This shape can be adjusted as well. The corresponding elongated slots also can be varied in quantity, size, and shape in terms of length and height of the opening. In the description below, the slots are shown to at least partially close the height at a middle portion of the slot. This closing is referred to as a collapsing feature. As used herein, the term collapse simply means the top and bottom portions can move locally closer together at those locations as the fastener is tightened. The term collapse simply means at these locations the height of the slot at the mid location decreases by the compressive tightening of the fastener. This decrease can be adjusted from a very small few thousandths of an inch to larger amounts wherein the slot locally collapses to allow the top and bottom portions to contact each other if so desired. This adjustment can be achieved by varying the resilient washer structural dimensions or by selecting different materials having specific stiffness or hardness. In that regard, the resilient washer can be a metal such as, by way of example, steel, stainless steel, titanium, aluminum, brass, copper, nickel or alloys of any of these metals. Alternatively, the resilient washer can be made of a synthetic polymer such as a plastic or elastomeric material. Examples of such washers could be PEEK, ABS, polyethylene, polycarbonate or any other suitable material of sufficient stiffness to achieve the desired compressive spring force, to aid in anti-loosening of the fastener, to act as a visual indicator that the washer and fastener have been desirably compressed. The following description exemplifies embodiments of the present invention that are useful in a number of applications such as construction manufacturing and assembly of devices and apparatus, and even in medical applications requiring the use of fasteners to be used in bone repairs.

With reference to FIGS. 1-5, the washer of the present invention is illustrated. The washer 10 has an opening 12 through which a fastener can pass. The washer 10, as shown in FIG. 1, has an upper fastener interfacing section or bowl 20 and a lower structure interfacing section or bowl 30, the lower structure interfacing section or bowl 30 is inverted relative to the upper fastener interfacing section or bowl 20. Interposed between the upper fastener interfacing section or bowl 20 and lower structure interfacing section or bowl 30 is a resilient middle portion 40. The resilient middle portion 40, as illustrated, has a plurality of columns 42 spaced by elongated enclosed slotted openings 44 extending around the periphery of the middle portion 40. As shown, the columns 42 are somewhat arch shaped at the top and bottom creating oval ends of the enclosed slotted openings 44. The elongated enclosed slotted openings 44, as shown in FIGS. 1-5 are provided as four enclosed slotted openings 44 and four columns 42. It is understood that fewer slotted openings and columns can be used, such as three slotted openings and three columns, or more columns with associated slotted openings could be provided. It is possible that the columns can be designed to be somewhat fragile so that they can locally collapse or bend as well. However, in the present invention washer 10, the columns 42 are shown rather substantial such that the bending is locally directed to a mid-portion of the enclosed slotted openings 44 as will be discussed later when used with an exemplary fastener, as illustrated in FIGS. 6-8C.

Figure 2:
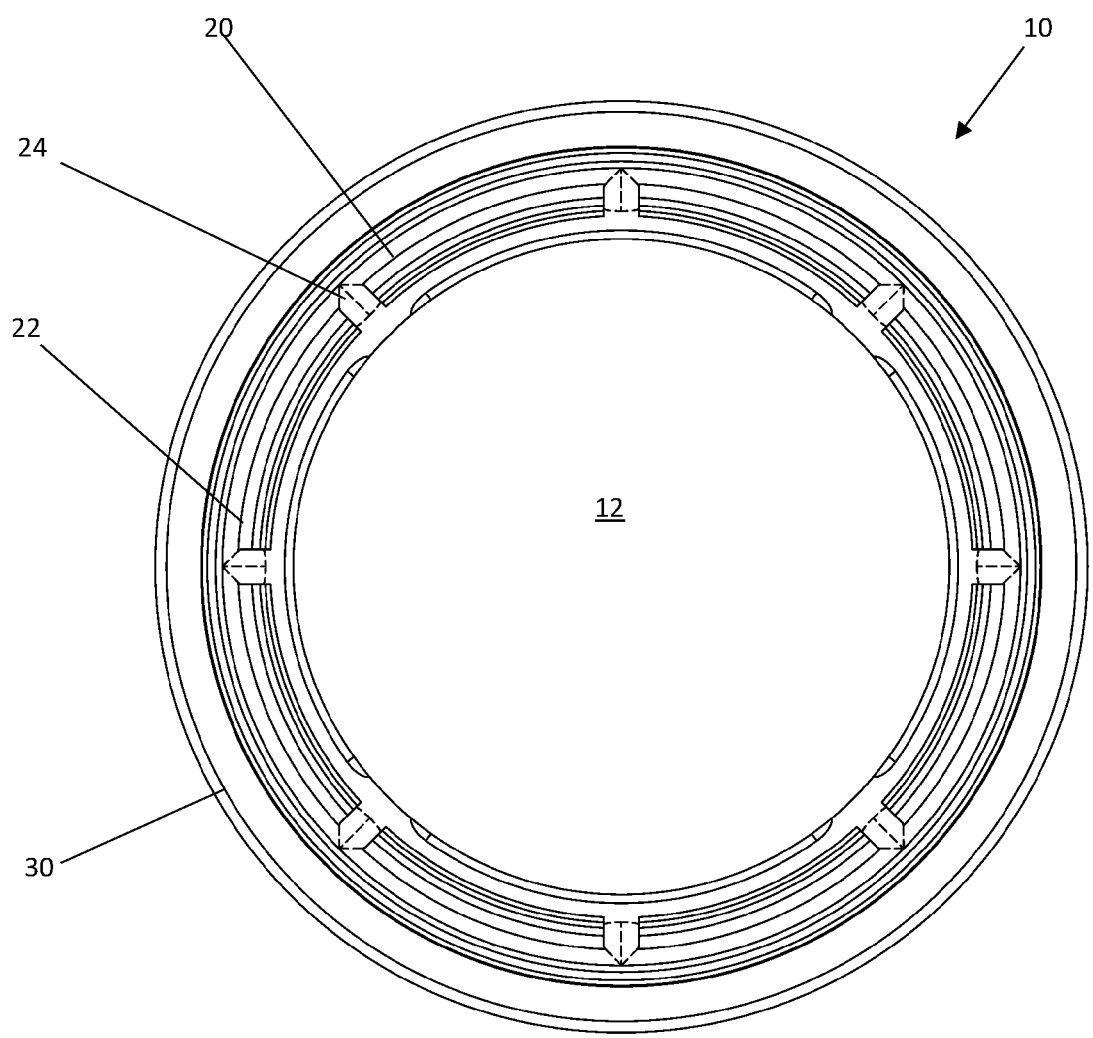
FIG. 2 is a top plan view of the resilient washer of FIG. 1.

With reference to FIG. 2, the center opening 12 of the resilient washer 10 is shown clearly. The upper fastener interfacing section or bowl 20 has a plurality of grooves 24 shown in an annular rim 22. The grooves 24 are shown being equally spaced around the circumference of the center opening 12. As illustrated, there are 8 grooves 24. The annular rim and grooves form a number of spring-like tabs which aid in the retention of the washer to a fastener. As shown, the upper fastener interfacing section or bowl 20 has an outside diameter smaller than the lower structure interfacing section or bowl 30. The upper fastener interfacing section or bowl 20 has an interior surface configured to receive a head of a fastener.

Figure 3:
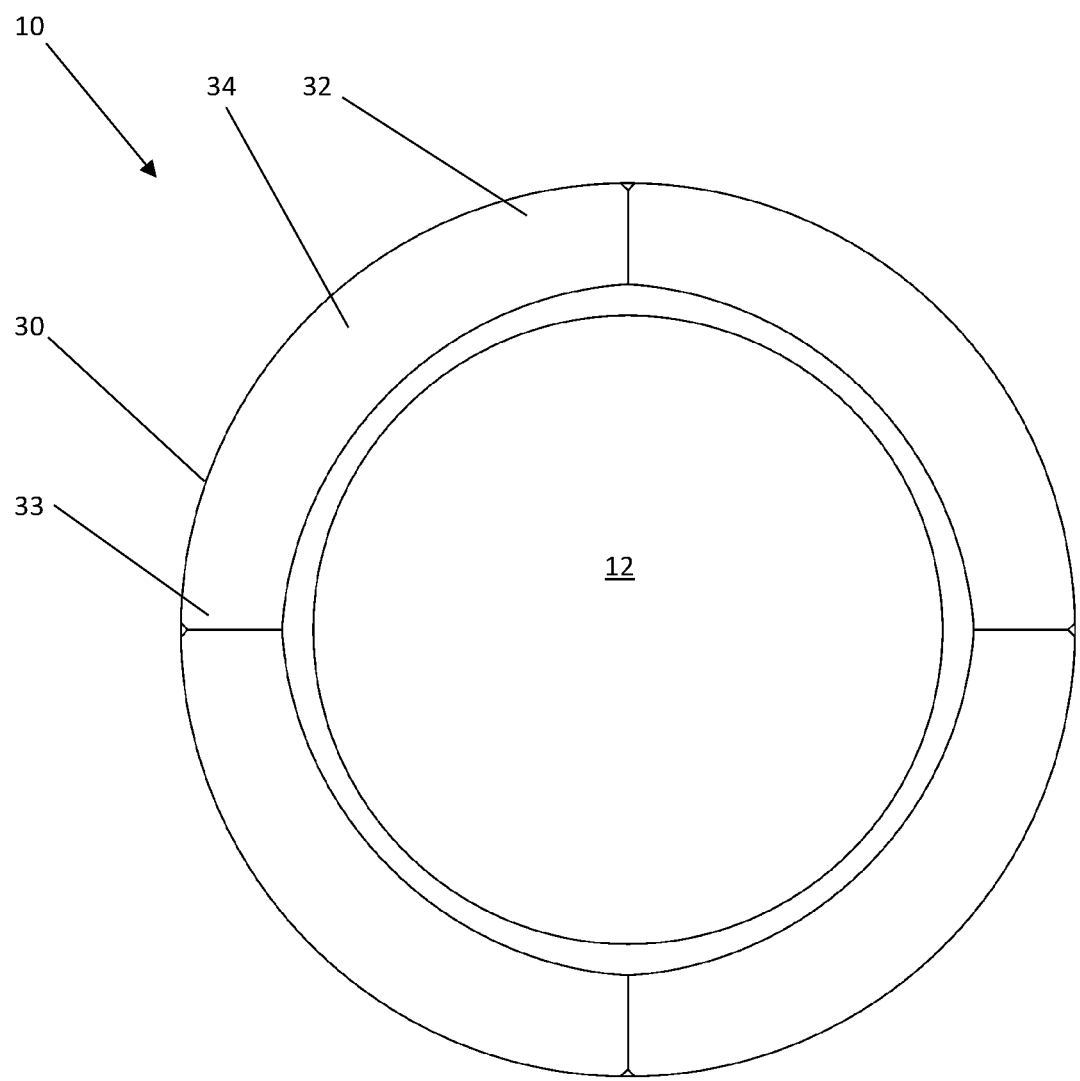
FIG. 3 is a bottom plan view of the resilient washer of FIG. 1.

With reference to FIG. 3, a bottom plan view of the resilient washer 10 is illustrated with the central opening 12 shown clearly through the lower structure interfacing section or bowl 30. The lines extending from the outer circumference of the lower structure interfacing section or bowl 30 towards the inner diameter of the lower structure interfacing section or bowl 30 represent the peaks 33. Peaks 33 lie between troughs 34 of the present invention. As shown, the end 32 of the bottom bowl is configured to abut against the surface against which the resilient washer 10 is being attached.

Figure 4:
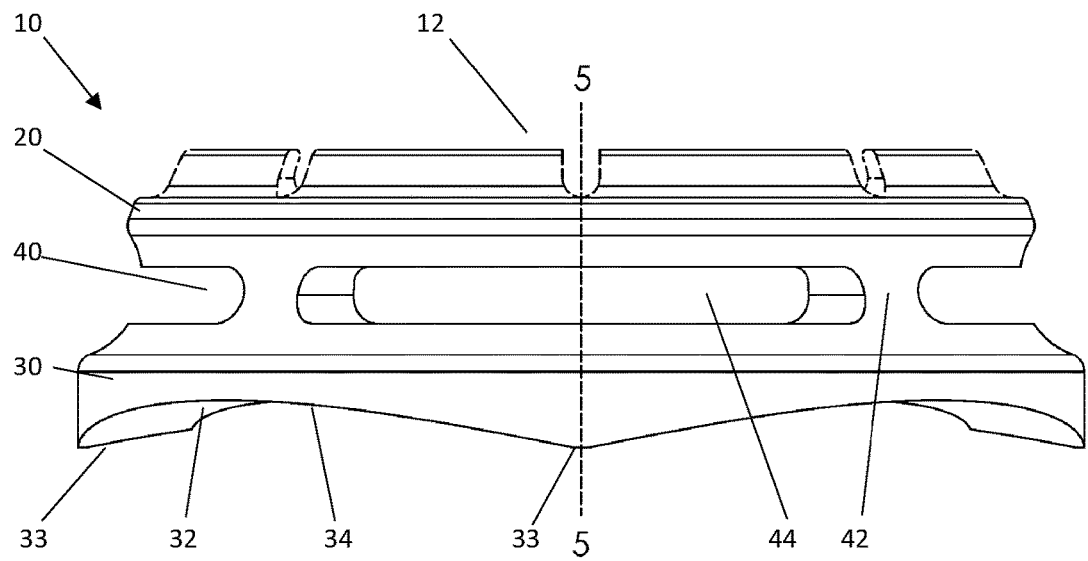
FIG. 4 is a side plan view of the resilient washer of FIG. 1.

With reference to FIG. 4, a side view of the resilient washer 10 is illustrated. In this side view, it is clear that the middle portion 40 has columns 42 equally spaced. Each pair of columns 42 having an elongated slotted opening 44 extending therebetween. As shown, the peaks 33 at the bottom end 32 of the lower structure interfacing section or bowl 30 are clearly visible.

Figure 5:
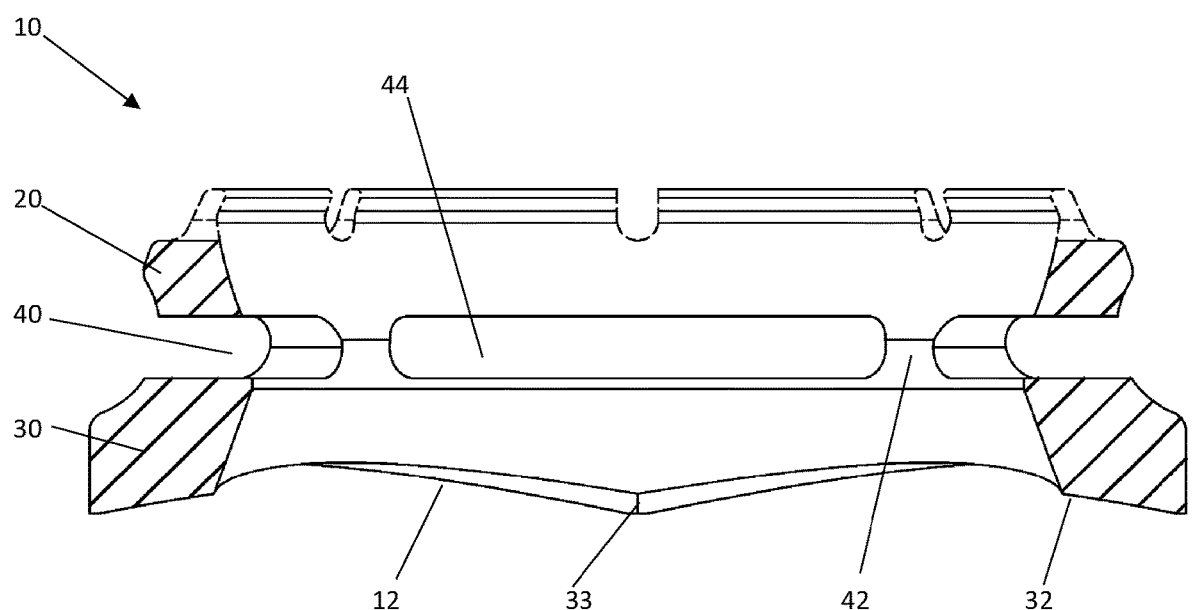
FIG. 5 is a cross sectional plan view of the resilient washer of FIG. 4.

With reference to FIG. 5, a cross sectional view taken from FIG. 4 is illustrated, showing the peaks 33 lie directly below the midpoint of the slotted openings 44 between the columns 42. It is important this configuration be provided as it must be remembered that the peaks 33 of the bottom end 32 of the lower structure interfacing section or bowl 30 first contacts the exterior surface of a structure that is to be fastened. As shown, the end 32 is inclined slightly tapering upwardly toward the center of the opening 12 in such a fashion that the bottom end 32 first engages the surface to be contacted at the peaks 33 and then pushes against the exterior surface in such a way that the peaks 33 can embed into the surface acting as an anchor or, if the surface is hardened, the entire end 32 can slightly twist locally. This is best illustrated in FIGS. 6-8C.

Figure 6:
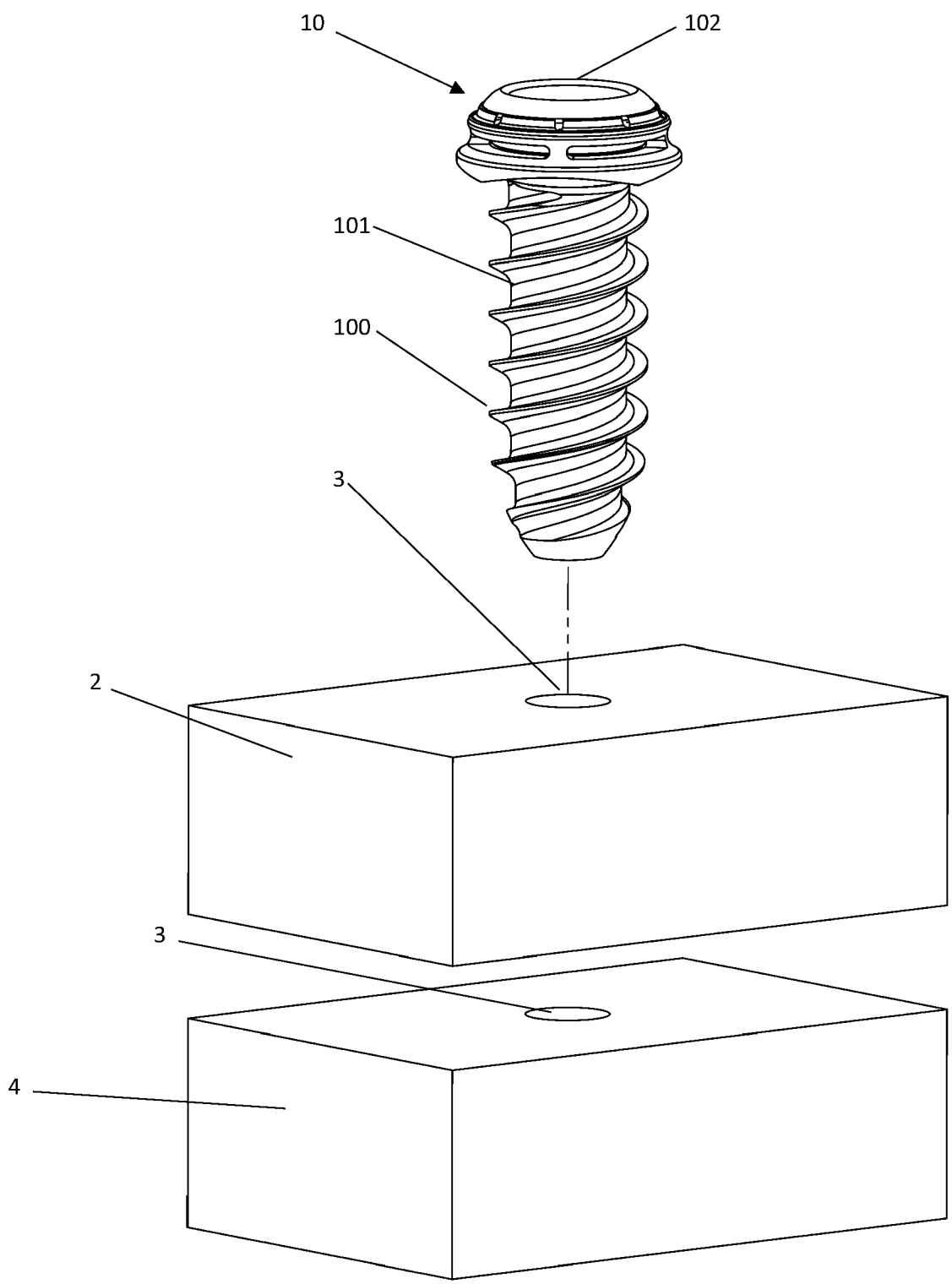
FIG. 6 is a perspective view of the resilient washer and an exemplary fastener prior to being inserted into two structures to be fastened together.

FIG. 6 shows a fastener 100 with a threaded shank 101 attached to a head 102 of the fastener. At a distal portion of the head 102 is the resilient washer 10 of the present invention. As illustrated, there is an upper block structure 2 and a lower block structure 4 each having a pre-drilled opening 3. It is understood that should a wood screw or self-drilling type fastener be used there would be no pre-drilled opening. However, in the exemplary embodiment, it is illustrated that not only are the openings 3 pre-drilled, but the block structures 2, 4 are slightly spaced. This situation would occur assuming that one was trying to join two materials that are spaced apart. For example, in a bone fracture, the bones may be spaced apart such that they need to be drawn tightly together in order to facilitate healing. In the case of bone where the outer surface is cortical bone and the interior surface is cancellous bone, it is important that the fastener be able to engage the different physiological structures of the bone so that it can make a secure tightening of the fracture bringing the bones closer together to facilitate healing.

Figure 7A:
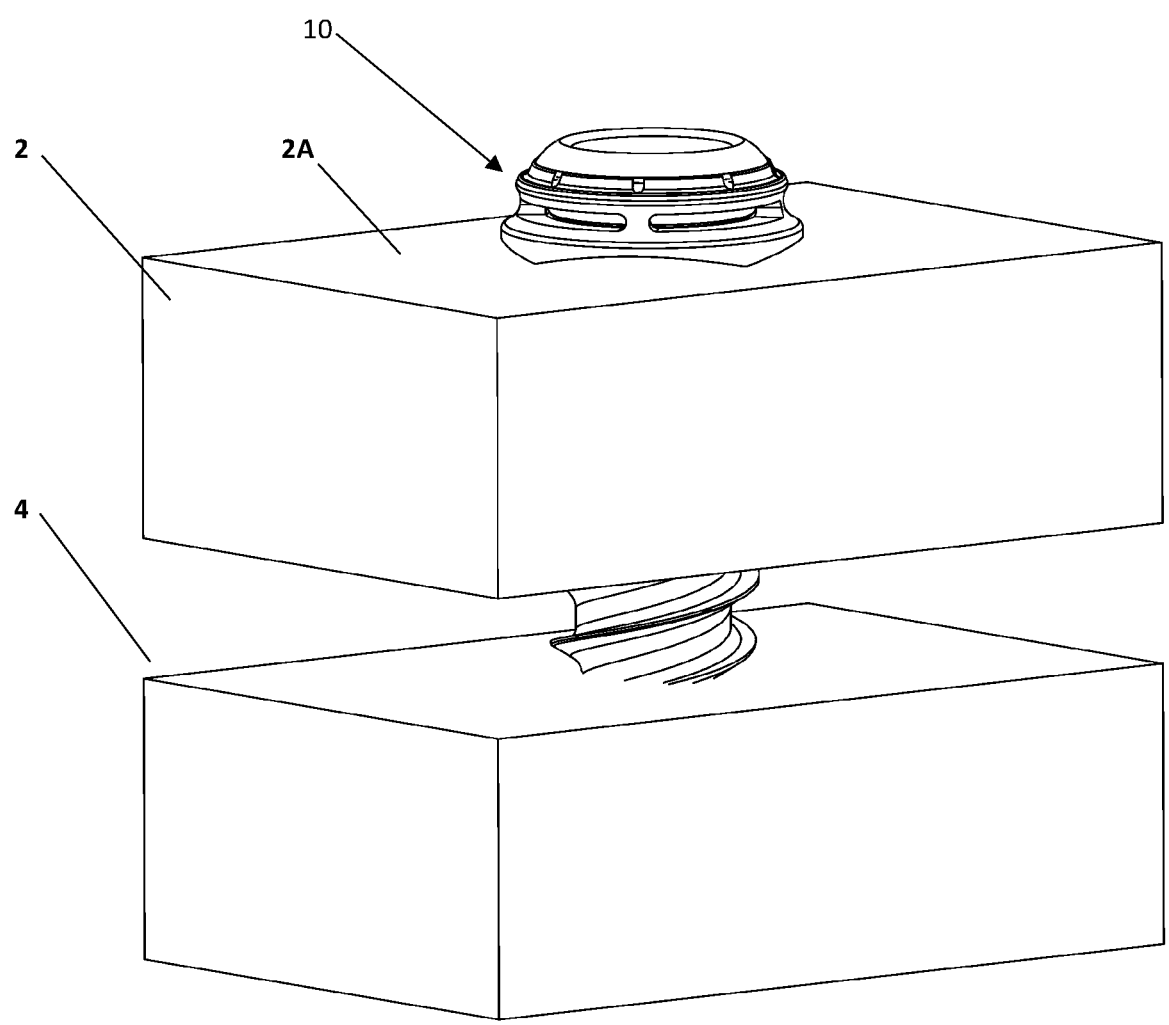
FIG. 7A is the perspective view taken from FIG. 6 showing the resilient washer and fastener assembly engaging the first and second structure to be fastened prior to tightening.
Figure 7B:
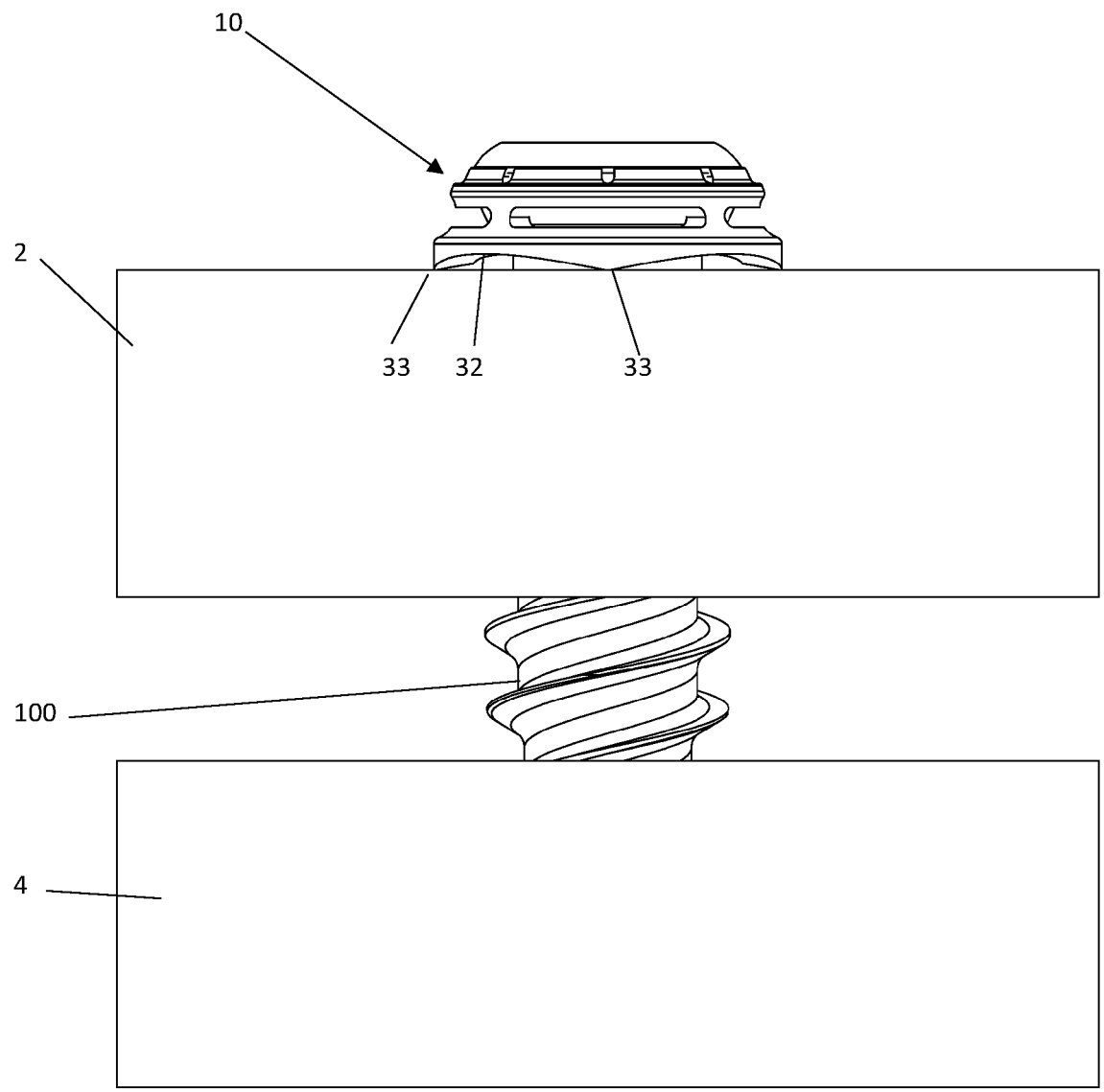
FIG. 7B is a plan side view taken from FIG. 7A.
Figure 7C:
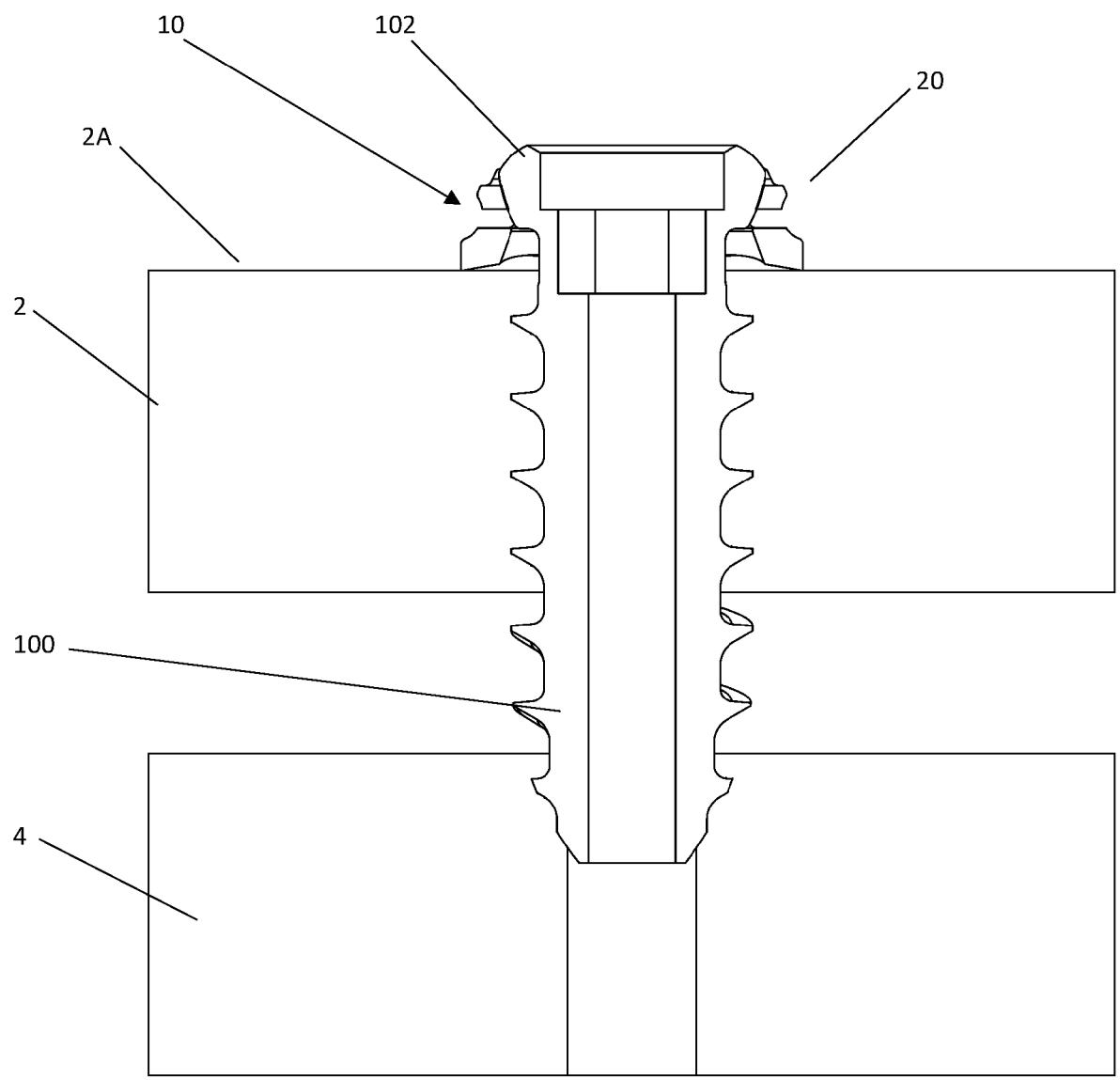
FIG. 7C is a cross sectional plan view taken from FIG. 7B.

As illustrated in FIG. 7A, the fastener 100 with resilient washer 10 is shown fully engaged in the first block structure 2 with the lower block structure 4 still being spaced apart. In this configuration, as shown in FIGS. 7A and 7B, it can be seen that the peaks 33 are initially contacting the exterior surface 2A of the block 2 at the end 32. This is also shown in the cross section of FIG. 7C. In this initial engagement, it is clear to see that the threaded fastener 100 has the threaded shank 101 engaged fully into the first block 2 and partially or initially engaged into the lower block 4 through the openings 3. As shown, the resilient washer 10 with the head 102 of the fastener 100 is fully supported by the upper fastener interfacing section or bowl 20. As shown, the head 102 of the fastener 100 has a curved contour and the interior surface of the upper fastener interfacing section or bowl 20 is similarly contoured with a curved interior surface. This curvature allows for rotation of the fastener 100 relative to the washer 10. Additionally, the fastener 100 can be inclined relative to the center axis of the washer 10, this is commonly referred to as polyaxial movement. This feature is beneficial in many occurrences. However, in the illustration, the washer 10 and fastener 100 are shown aligned along a common central axis.

Figure 8A:
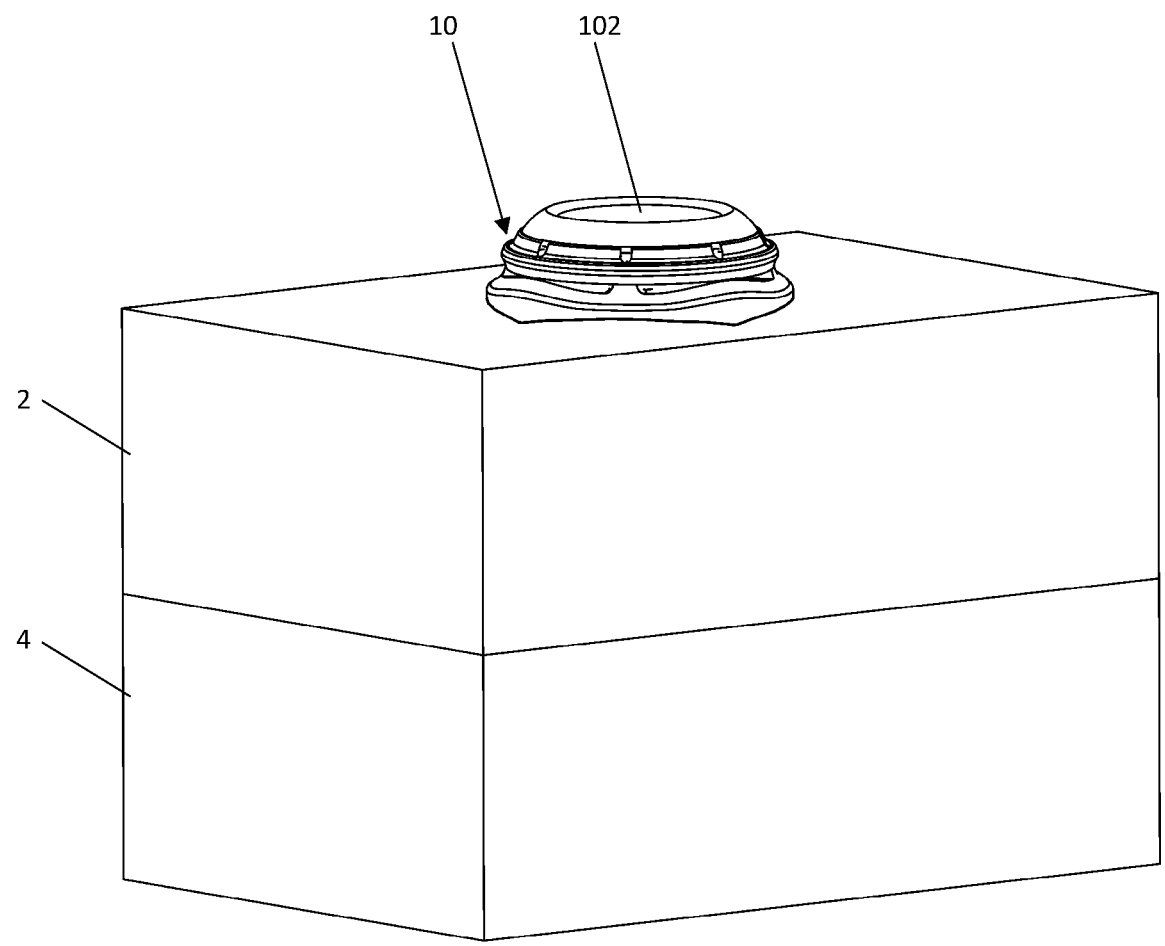
FIG. 8A is the perspective view of the resilient washer and fastener assembly after being tightened and fastening together the two structures.
Figure 8B:
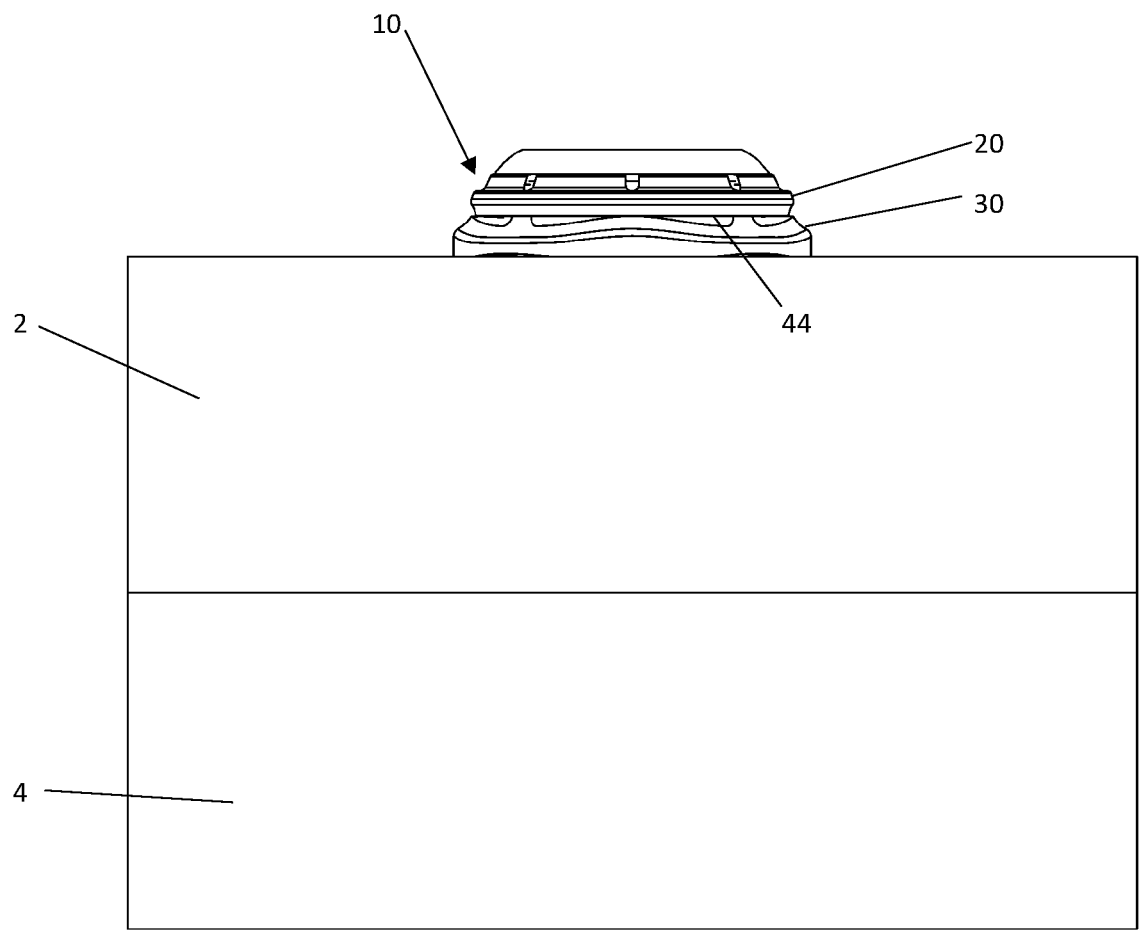
FIG. 8B is a plan side view taken from FIG. 8A.
Figure 8C:
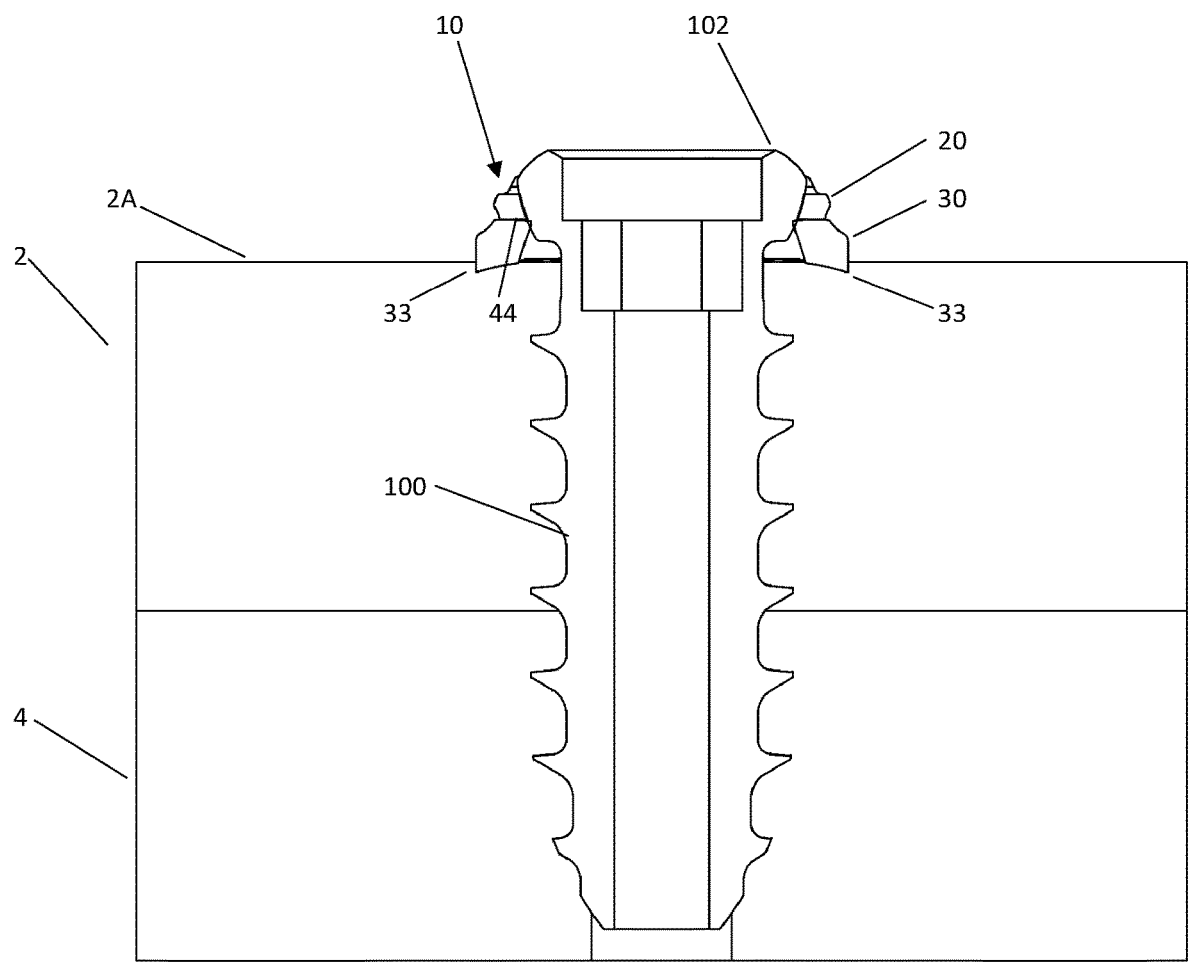
FIG. 8C is a cross sectional plan view taken from FIG. 8B.

With reference to FIG. 8A, the upper block structure 2 and lower block structure 4 are shown abuttingly engaged, held by the fastener 100 supported by the washer 10. In the illustration, the material exterior surface 2A into which the washer 10 is engaged is such that he peaks 33 are embedded into the upper structure 2. This is similarly shown in FIG. 8B. With reference to FIGS. 8A and 8B, it is important to note that at the resilient middle portion 40 of the washer 10, the slotted openings 44 collapse and are compressed such that the upper fastener interfacing section or bowl 20 is in very close proximity, if not touching, the lower structure interfacing section or bowl 30. This local collapsing occurs because the peaks 33 embedded in the material of the upper block structure 2 push upwardly causing the lower structure interfacing section or bowl 30 to flex or bend upward toward the upper fastener interfacing section or bowl 20 which is supporting the head 102 of the fastener 100. This creates a unique spring like feature that helps engage the fastener 100 when fully tightened into the upper and lower block structures 2, 4.

This is also shown well in cross sectional view 8C where the fastener 100 is shown with the head 102 pushing against the interior of the upper fastener interfacing section or bowl 20 in such a fashion that the upper fastener interfacing section or bowl 20 is pushed towards the lower structure interfacing section or bowl 30 which has been deflected upwardly due to the location of the peaks 33 being centered under the slotted openings 44. Slotted openings 44 are shown almost completely collapsed as best shown in cross sectional view 8C. Furthermore, the peaks 33 are shown partially embedded into the exterior surface 2A of the upper block structure 2. In the illustrated embodiment of the present invention, this means 4 peaks 33 are locally embedded into and through the exterior surface 2A penetrating and creating a resistance to rotation. This resistance to rotation and spring like effect creates a locking feature for the resilient washer 10 to hold the fastener 100 in position.

It is believed that the local collapsing at multiple points creates a superior anti-rotation and anti-loosening feature of the present invention that is particularly useful in materials that have a potentially hard outer surface and a softer interior surface such as bone. Additionally, it is believed that the local collapsing at multiple points creates a compressive load on the exterior surface that creates a spring like force on the fastener to help hold separate structures together. The present invention exemplary embodiment is shown with a threaded fastener with a hemispherical head or semi-hemispherical head allowing for polyaxial movement, however, it is understood that this invention will work equally well with alternate geometries such as a washer having a conical interior surface for holding the fastener head and a complimentary conical head of a fastener or screw.

Alternatively, the fastener may not be threaded, but rather could be a nail type fastener. In the case of a nail, the washer would be put against the head of the nail and could have a counterbore recess allowing the head to lie flush when the nail with the washer is inserted into a board. The nail may have flutes along the shank, this would create a similar locking action of the washer and the nail. It is therefore understood that the present invention washer with its local collapsing capability can be used on multiple structures for multiple purposes. Besides bone screw applications, it could be used in any application securing any two material together using screws, bolts, rivets, nails, etc. For example, it could be used for roofing, drywall or any other applications in which a compressive load on the exterior surface is achieved with multiple peaks embedded in the exterior surface to prevent rotation and a collapsible middle portion to create a spring like force on the fastener to help hold the structures together.

The resilient washer of the present invention allows for several unique techniques of fastening as described in the following methods.

A method of tightening or securing a fastener using a torque or force has the steps of providing a resilient washer and a fastener. The resilient washer having a central opening for receiving the fastener in an upper fastener interfacing section or bowl, a lower structure interfacing section or bowl and a resilient middle portion connecting the upper fastener interfacing section or bowl and the lower structure interfacing section or bowl wherein the resilient middle portion is configured to be locally collapsed at a collapsing force when a fastener in the central opening of the resilient washer is tightened or inserted into a structure; and tightening or inserting the fastener into a structure by torqueing or otherwise applying an insertion force sufficient to locally collapse the middle portion.

The fastener is a threaded screw and the step of tightening is achieved by torqueing the screw into the structure creating the collapsing force sufficient to locally collapse the middle portion, the force corresponding to the applied fastening torque of a fastener driver. When the collapsing force is achieved, the method further has the step of visually observing the locally collapsed middle portion of the resilient washer; and stopping driving the fastener into the structure.

The method wherein the fastener is a nail and the step of inserting includes driving the nail into the structure with a collapsing force sufficient to locally collapse the middle portion of the resilient washer and to seat the nail into the structure. The method further includes driving the nail into the structure and through the opening of the resilient washer by using a nail gun, the nail gun being set to a collapsing force to seat the nail and locally collapse the middle portion of the resilient washer. When the collapsing force is achieved, the method further comprises the step of visually observing the locally collapsed middle portion of the resilient washer; and stopping driving the fastener into the structure. The step of providing the resilient washer includes the step of making and fabricating by machining, molding, casting the resilient washer using metal or plastics sized to have the middle portion of the resilient washer locally collapse at a collapsing force. The collapsing force is selected for the structure and size of the fastener, the collapsing force being higher or lower dependent on the application to be fastened.

A method of tightening or securing a fastener using a visual indicator has the steps of providing a resilient washer and a fastener, the resilient washer having a central opening for receiving the fastener in an upper fastener interfacing section or bowl, a lower structure interfacing section or bowl and a resilient middle portion connecting the upper fastener interfacing section or bowl and the lower structure interfacing section or bowl wherein the resilient middle portion is configured to be locally collapsed at a collapsing force when a fastener in the central opening of the resilient washer is tightened or inserted into a structure; tightening or inserting the fastener into a structure by torqueing or otherwise applying an insertion force sufficient to locally collapse the middle portion; visually observing the middle portion of the resilient washer to see the local collapsing; and stopping the tightening or insertion when the collapsing occurs. Upon completion of tightening or inserting the fastener, the resilient washer when collapsed provides anti-rotation of the fastener relative to the structure, anti-loosening and applies a compressing spring force between the fastener and the structure.

The method wherein the fastener is a bone screw or fastener used in a medical or medical implant procedure and the method of using a visual indicator further comprises the step of imaging the bone screw or fastener as the fastener is being tightened or inserted to observe an occurrence of the localized collapsing of the middle portion; and stopping the tightening or inserting upon viewing the localized collapse on an imaging screen.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A resilient washer having a one-piece washer body, the washer body comprising:

a central opening;
    an upper fastener interfacing section or bowl, wherein the upper fastener interfacing section or bowl is annular and has a concavity for holding a head of the fastener, wherein the concavity is of a hemispherical shape;
    a lower structure interfacing section or bowl;
    a resilient middle portion connecting the upper fastener interfacing section or bowl and the lower structure interfacing section or bowl, wherein the middle portion has a plurality of columns connecting the upper fastener interfacing section or bowl and lower structure interfacing section or bowl, wherein each of the plurality of columns is spaced by an enclosed slotted opening forming a plurality of enclosed slotted openings, the resilient middle portion configured to be locally collapsed when a fastener in the central opening is tightened or inserted into a structure.

2. The resilient washer of claim 1 wherein the concavity has a smooth surface to allow polyaxial movement of a fastener.

3. The resilient washer of claim 1 wherein the lower structure interfacing section or bowl is annular.

4. The resilient washer of claim 3 wherein the lower structure interfacing section or bowl has a distal end for engaging a surface of a structure to be fastened.

5. The resilient washer of claim 4 wherein the distal end is contoured having a plurality of elongated peaks spaced by shallow troughs wherein the peaks first contact the surface of the structure to be fastened.

6. The resilient washer of claim 5 wherein the distal end is tapered or inclined toward the central opening.

7. The resilient washer of claim 1 wherein upon tightening of the fastener to the structure a portion of each slotted opening locally collapses bringing the lower structure interfacing section or bowl and upper fastener interfacing section or bowl closer in proximity.

8. The resilient washer of claim 7 wherein each of the slotted openings extends arcuately between columns and the collapse of each of the slotted openings occurs midway between the columns.

9. The resilient washer of claim 5 wherein upon tightening of the fastener to the structure a portion of each slotted opening locally collapses bringing the lower structure interfacing section or bowl and upper fastener interfacing section or bowl closer in proximity.

10. The resilient washer of claim 9 wherein each of the slotted openings extends arcuately between columns and the collapse of each of the slotted openings occurs midway between the columns.

11. The resilient washer of claim 9 wherein each peak of the distal end is located midway between a pair of adjacent columns and centered under a slotted opening.

12. The resilient washer of claim 10 wherein each column is positioned above a midway location of each shallow trough.

13. The resilient washer of claim 12 wherein the resilient washer has four columns and four slotted openings in the middle portion.

14. The resilient washer of claim 1 wherein the washer body is made of metal.

15. The resilient washer of claim 14 wherein the metal is one of steel, stainless steel, titanium, aluminum or alloys of each.

16. The resilient washer of claim 1 wherein the washer body is made of a plastic.

17. The resilient washer of claim 1 wherein the upper fastener interfacing section or bowl has an annular rim at a proximal end with a plurality of spaced grooves.

18. A method of tightening or securing a fastener using a torque or force comprises the steps of:
providing a resilient washer and a fastener, the resilient washer having a central opening for receiving the fastener in an upper fastener interfacing section or bowl, wherein the upper fastener interfacing section or bowl is annular and has a concavity for holding a head of the fastener, wherein the concavity is of a hemispherical shape; a lower structure interfacing section or bowl and a resilient middle portion connecting the upper fastener interfacing section or bowl and the lower structure interfacing section or bowl, wherein the middle portion has a plurality of columns connecting the upper fastener interfacing section or bowl and lower structure interfacing section or bowl, wherein each of the plurality of columns is spaced by an enclosed slotted opening forming a plurality of enclosed slotted openings, wherein the resilient middle portion is configured to be locally collapsed at a collapsing force when a fastener in the central opening of the resilient washer is tightened or inserted into a structure; and
tightening or inserting the fastener into a structure by torqueing or otherwise applying an insertion force sufficient to locally collapse the middle portion.

19. The method of claim 18 wherein the fastener is a threaded screw and the step of tightening is achieved by torqueing the screw into the structure creating the collapsing force sufficient to locally collapse the middle portion, the force corresponding to the applied fastening torque of a fastener driver.

20. The method of claim 19 wherein when the collapsing force is achieved, the method further comprises the step of:
visually observing the locally collapsed middle portion of the resilient washer; and
stopping driving the fastener into the structure.

21. The method of claim 18 wherein the fastener is a nail and the step of inserting includes driving the nail into the structure with a collapsing force sufficient to locally collapse the middle portion of the resilient washer and to seat the nail into the structure.

22. The method of claim 21 wherein the method further includes driving the nail into the structure and through the opening of the resilient washer by using a nail gun, the nail gun being set to a force to seat the nail and locally collapse the middle portion of the resilient washer.

23. The method of claim 22 wherein when the collapsing force is achieved, the method further comprises the step of:
visually observing the locally collapsed middle portion of the resilient washer; and
stopping driving the fastener into the structure.

24. The method of claim 18 wherein the step of providing the resilient washer includes the step of making and fabricating by machining, molding, casting the resilient washer using metal or plastics sized to have the middle portion of the resilient washer locally collapse at a collapsing force.

25. The method of claim 24 wherein the collapsing force is selected for the structure and size of the fastener, the collapsing force being higher or lower dependent on the application to be fastened.

26. A method of tightening or securing a fastener using a visual indicator comprises the steps of:
providing a resilient washer and a fastener, the resilient washer having a central opening for receiving the fastener in an upper fastener interfacing section or bowl, wherein the upper fastener interfacing section or bowl is annular and has a concavity for holding a head of the fastener, wherein the concavity is of a hemispherical shape; a lower structure interfacing section or bowl and a resilient middle portion connecting the upper fastener interfacing section or bowl and the lower structure interfacing section or bowl, wherein the middle portion has a plurality of columns connecting the upper fastener interfacing section or bowl and lower structure interfacing section or bowl, wherein each of the plurality of columns is spaced by an enclosed slotted opening forming a plurality of enclosed slotted openings, wherein the resilient middle portion is configured to be locally collapsed at a predetermined force when a fastener in the central opening of the resilient washer is tightened or inserted into a structure;
tightening or inserting the fastener into a structure by torqueing or otherwise applying an insertion force sufficient to locally collapse the middle portion;
visually observing the middle portion of the resilient washer to see the local collapsing; and
stopping the tightening or insertion when the collapsing occurs.

27. The method of claim 26 wherein upon completion of tightening or inserting the fastener, the resilient washer when collapsed provides anti-rotation of the fastener relative to the structure, anti-loosening and applies a compressing spring force between the fastener and the structure.

28. The method of claim 26 wherein the fastener is a bone screw or fastener used in a medical implant procedure and the method of using a visual indicator further comprises the step of:
imaging the bone screw or fastener as the fastener is being tightened or inserted to observe an occurrence of the localized collapsing of the middle portion; and
stopping the tightening or inserting upon viewing the localized collapse on an imaging screen.

* * * * *

UNITED STATES PATENT AND TRADEMARK OFFICE
CERTIFICATE OF CORRECTION

| | | |
|---|---|---|
| PATENT NO. | : 11,446,071 B2 | |
| APPLICATION NO. | : 16/983035 | |
| DATED | : September 20, 2022 | |
| INVENTOR(S) | : Eric Linder and Ryan Heskett | |

It is certified that error appears in the above-identified patent and that said Letters Patent is hereby corrected as shown below:

On the Title Page

Correct the attorney, agent's name from:
"Davikd L King"
To read:
(74) Attorney, Agent, or Firm - David L. King Signed and Sealed this
Eighteenth Day of October, 2022

Katherine Kelly Vidal
*Director of the United States Patent and Trademark Office*